United States Patent [19]

Yoshioka et al.

[11] Patent Number: 4,997,922
[45] Date of Patent: Mar. 5, 1991

[54] ANTHRACYCLINE DERIVATIVES

[75] Inventors: Takeo Yoshioka, Ayase; Toshio Tsuchida, Yokohama; Ryoichi Miyata, Fujisawa; Hiroshi Tone, Yokohama; Rokuro Okamoto, Fujisawa, all of Japan

[73] Assignee: Sanraku Incorporated, Tokyo, Japan

[21] Appl. No.: 297,938

[22] Filed: Jan. 17, 1989

[51] Int. Cl.$^5$ ............................................. C07H 15/22
[52] U.S. Cl. .................................................. 536/6.400
[58] Field of Search ........................................ 536/6.4

[56] References Cited
U.S. PATENT DOCUMENTS
4,393,052  7/1983  Bargiotti et al. ..................... 536/6.4

FOREIGN PATENT DOCUMENTS
0039060A1  11/1981  European Pat. Off. .
2381060    9/1978   France ..................... 15/24
WO86/0073  1/1986   PCT Int'l Appl. .................... 15/252

OTHER PUBLICATIONS
Morrison, *Organic Chemistry*, 3rd ed., (1979) pp. 190 and 663, published by Allyn and Bacon, Inc.

Primary Examiner—Johnnie R. Brown
Assistant Examiner—Elli Peselev
Attorney, Agent, or Firm—Wenderoth, Lind & Ponack

[57] ABSTRACT

14-Trifluoromethanesulfonyloxydaunomycin represented by the following formula

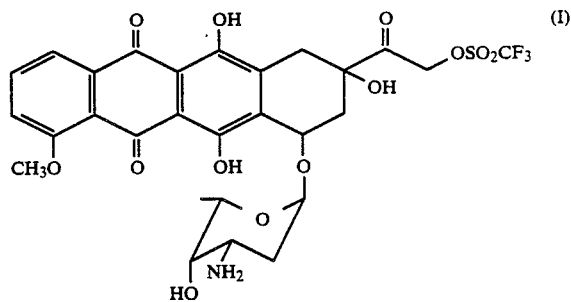

and its salt. This compound is useful as an intermediate for production of adriamycin.

1 Claim, No Drawings

ANTHRACYCLINE DERIVATIVES

This invention relates to novel anthracycline derivatives, and more specifically, to 14-trifluoromethanesulfonyloxydaunomycin represented by the following formula (I) and its salts, a process for production thereof, and to a process for production of adriamycin and its salts from the compound of formula (I).

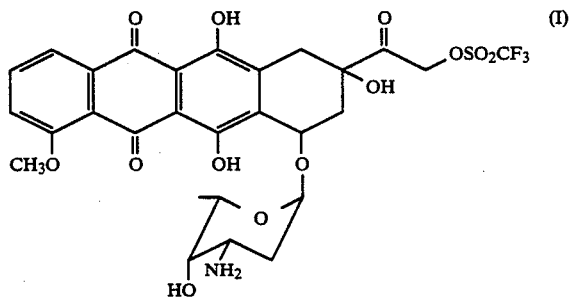

Adriamycin is a substance which has antibacterial activity and antitumor activity and is useful as an antitumor agent. Various methods of its synthesis are known. For example, U.S. Pat. No. 3,803,124 (corresponding to Japanese Patent Publication No. 46597/1972) discloses a method of producing adriamycin which comprises reacting daunomycin with a halogen, reacting the resulting 14-halodaunomycin with an alkali metal acetate in a polar solvent, and hydrolyzing the resulting 14-acetoxydaunomycin under alkaline conditions. However, this method involving hydrolyzing the 14-acetoxydaunomycin under alkaline conditions has the serious defect that since the resulting adriamycin is unstable to alkali, it undergoes decomposition, and its yield decreases.

The present inventors extensively worked on a process for producing adriamycin which is free from the above defect, and have found that novel 14-trifluoromethanesulfonyloxydaunomycin represented by formula (I) above obtained by reacting a 14-halodaunomycin with a metal trifluoromethanesulfonate can be hydrolyzed under acidic conditions, and adriamycin can be produced in a high yield.

Thus, the present invention provides 14-trifluoromethanesulfonyloxydaunomycin of formula (I) and its salts as novel substances.

The salts of the compound (I) may include, for example, inorganic acid salts such as a hydrochloride, hydrobromide or hydroiodide, and organic salts such as a trifluoromethanesulfonate or trifluoroacetate.

The compound of formula (1) can be produced by reacting a 14-halodaunomycin represented by the following formula

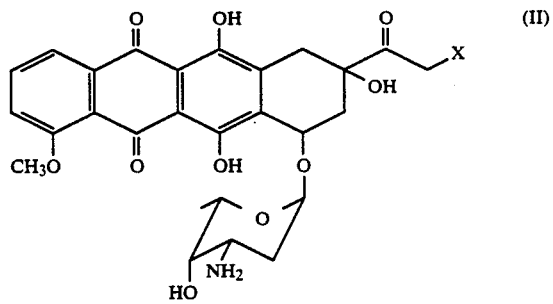

wherein X represents a halogen atom, or its salt with a metal trifluoromethanesulfonate.

The reaction of the compound of formula (II) or its salt (such as its hydrochloride or hydrobromide) with the metal trifluoromethanesulfonate can be carried out usually in a polar organic solvent inert to the reaction, such as dimethylformamide or dimethyl sulfoxide, preferably the former, at a temperature in the range of about 0° C. to about 70° C., preferably room temperature.

The amount of the metal trifluoromethanesulfonate relative to the compound of formula (II) or its salt is not particularly limited. Its suitable amount is generally 1 to 5 moles, preferably 2 to 4 moles, per mole of the compound of formula (II) or its salt.

The compound of formula (II) used as the starting material in the above reaction is a known compound, and can be easily produced by methods which are described, for example, in U.S. Pat. No. 3,803,124 (Japanese Patent Publication No. 46597/1972), U.S. Pat. No. 4,225,589 (Japanese Patent Publication No. 26529/1979), Japanese Patent Publication No. 13558/1982, and U.S. Pat. No. 4,360,664 (Japanese Patent Publication No. 59719/1987).

Silver trifluoromethanesulfonate is most preferred as the metal trifluoromethanesulfonate to be reacted with the compound of formula (II). Other metal salts such as copper, tin, lithium, potassium and sodium trifluoromethanesulfonates may also be used.

The resulting compound of formula (I) or its salts may be separated and purified from the reaction mixture by known means such as chromatography, crystallization or precipitation. Alternatively, it may be subjected to a hydrolysis step to be described below without separation and purification.

The resulting compound of formula (I) or its salt can be converted to adriamycin or its salt in high yields by hydrolysis under acidic conditions.

The hydrolysis of the compound of formula (I) or its salt can be carried out by maintaining the compound of formula (I) at a temperature of about 10° C. to about 60° C., preferably at room temperature to about 50° C., in water, an aqueous buffer solution or a mixture of water and a water-miscible organic solvent.

Desirably, the pH of the aqueous medium at the time of hydrolysis is maintained generally at 2 to 6.5. Since an aqueous solution of the compound of formula (I) or its salt is usually acidic with a pH in the range of 2.0 to 2.4 (although this depends upon the type of the salt), it is not particularly necessary to adjust the pH of the aqueous solution at the time of hydrolysis. As required, a pH adjusting agent such as sodium hydroxide, potassium hydroxide, sodium hydrogen carbonate, sodium carbonate or sodium phosphate or an aqueous buffer solution may be used to adjust the pH of the aqueous medium to the above preferred range.

The hydrolysis can be terminated usually in about 10 to 40 minutes under these conditions. After the hydrolysis, the resulting adriamycin or its salt may be isolated and purified from the reaction mixture by known means such as extraction and crystallization.

The resulting adriamycin may be converted into a salt by treating it with a pharmaceutically acceptable acid such as hydrochloric or hydrobromic acid.

The following examples illustrate the present invention more specifically.

EXAMPLE 1

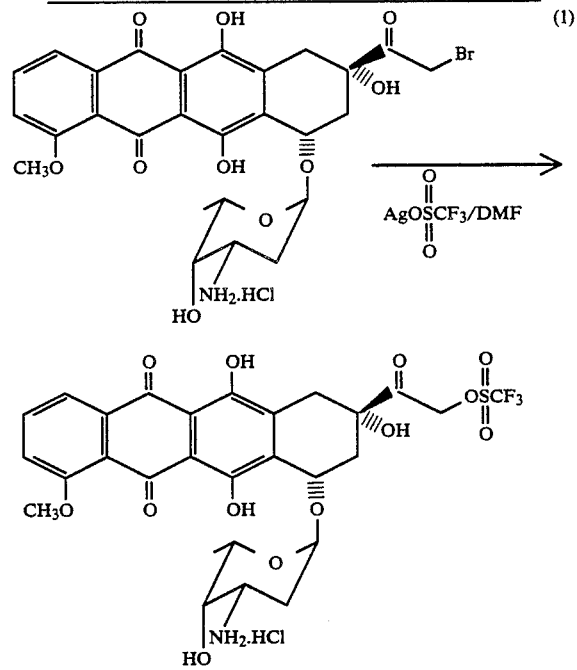

In a nitrogen atmosphere, 0.5995 g (2.333 mmoles) of silver trifluoromethanesulfonate was added to a solution in 10 ml of DMF of 0.500 g (0.777 mmole) of 14-bromodaunomycin hydrochloride prepared by the method described in Example 2 of U.S. Pat. No. 4,360,664 in a brown vessel, and the mixture was stirred overnight at room temperature. A solid (AgBr) which precipitated in the reaction mixture was separated by filtration and washed with DMF. The filtrate and the washing were combined, and concentrated under reduced pressure. Chloroform was added to the concentrate, and the mixture was vigorously stirred. Ultrasonic waves were applied to disperse the insoluble matter and precipitate it. The precipitate was separated by filtration, washed with chloroform, and dried to give 0.5606 g (yield quantitative) of 14-trifluoromethanesulfonyloxydaunomycin hydrochloride.

Physicochemical properties of 14-trifluoromethanesulfonyloxydaunomycin hydrochloride Rf value: 0.40 (TLC plate: Merck Art 5715; development system: $CHCl_3/CH_3OH/AcOH=20/6/1$)

$IR\nu_{max}^{KBr}$ cm$^{-1}$: 3420 (OH, NH$_2$), 1715 (C=O), 1615, 1580 (C=O), 1270, 1265, 1170 ($-OSO_2CF_3$)

$^1$H-NMR δppm (DMSO-d$_6$/TMS): 1.17(3H, d, J=6.5 Hz, H-6'), 1.68(1H, dd, J=11.8 Hz, 3.4 Hz, H-2'e), 1.90(1H, broad t, J=11.8 Hz, H-2'a), 2.09(1H, dd, J=13.3 Hz, 5.7 Hz, H-8a), 2.29(1H, broad d, J=13.3 Hz, H-8e), 2.83(3H, d, J=18.4 Hz, H-10a), 3.07(1H, d, J=18.4 Hz, H-10e), 3.34-3.40(1H, m, H-3'), 3.99(3H, s, O-CH$_3$), 4.19(1H, broad q, J=6.5 Hz, H-5'), 4.94-4.99(1H, m, H-7), 5.28-5.30(1H, m, H-1'), 5.25(1H, d, J=19.8 Hz, H-14), 5.33(1H, d, J=19.8 Hz, H-14), 5.58(1H, s, OH), 7.65-7.70(2H, m, H-2, H-3), 7.70-7.78(2H, broad s, NH$_2$), 7.92(1H, d, J=3.7 Hz, H-1), $^{13}$C-NMR δppm (DMSO-d$_6$): 20.6 C-6', 32.2 C-2', 35.7 C-10, 39.8 C-8', 50.7 C-3', 60.5 OCH$_3$, 68.9 C-14, 70.2 C-4', C-5', 73.4 C-7, 83.1 C-9, 103.2 C-1', 114.5, 114.6 (C-5a, C-11a), 122.9 C-3, 123.6 C-1, 123.7 C-4a, 137.6 C-10a, 138.4, 138.8 (C-12a, C-6a), 138.8 CF$_3$ J$_{CF}$=320.4 Hz, 140.1 C-2, 158.3 C-11, 159.9 C-6, 164.7 C-4, 190.1, 190.2 (C-5, C-12), 211.1 C-13

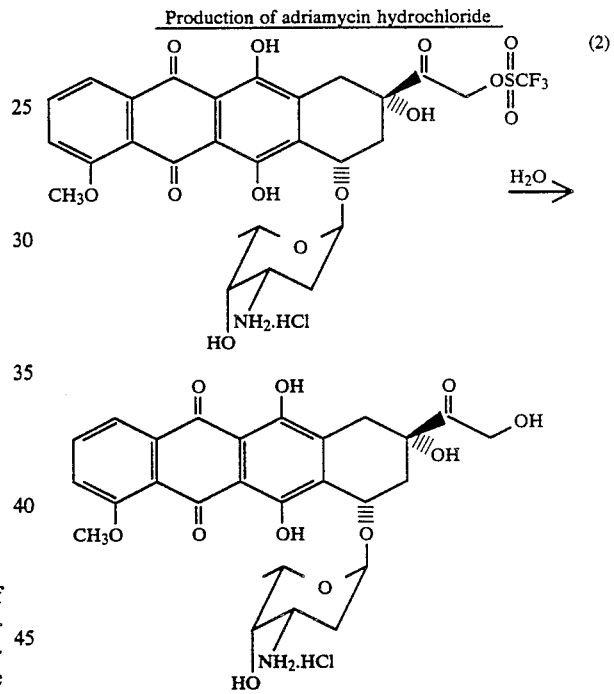

The 14-trifluoromethanesulfonyloxydaunomycin hydrochloride obtained in section (1) above (0.200 g, 0.2797 mmole) was dissolved (pH 2.4) in 20 ml of water, and the solution was maintained at room temperature for 25 hours with stirring to perform hydrolysis. The reaction mixture was diluted with 20 ml of water, and extracted with chloroform twice. Sodium chloride was added to the aqueous solution so as to provide an about 5% aqueous solution, and then chloroform and methanol (4:1) were added. The pH of the aqueous layer was adjusted to 7.4 with a saturated aqueous solution of sodium hydrogen carbonate. The aqueous layer was extracted with chloroform and methanol (4:1) four times, and the organic layer was washed with a saturated aqueous solution of sodium chloride, and dried over anhydrous sodium sulfate. Removing the solvent yielded 0.1074 g (yield 70.7%) of adriamycin (free form).

The adriamycin (free form) was dissolved in 10 ml of chloroform and methanol (10:1), and 0.234 ml of 1N-

HCl (in CH₃OH, f=1.013; 1.2 equivalents, 0.2374 mmole) was added. Concentrating the reaction mixture gave a precipitate. The concentrate was filtered. The filtrate was washed with chloroform/methanol (10:1) and further with chloroform, and dried to give 0.1023 g (HPLC relative purity: 94.1%; total yield from 14-bromodaunomycin hydrochloride 63.1%).

Physicochemical properties of adriamycin hydrochloride

Melting point: 203°-205° C. (decomp.)
$[\alpha]_D^{24}$: +250.8° (c=0.096, CH₃OH)
$\lambda_{max}$ (CH₃OH) nm: 531, 495, 480
IR$\nu_{max}^{KBr}$: 3370 (—OH, NH₂), 1725 (C=O), 1610, 1580 (C=O)
NMRδppm (DMSO-d₆/TMS): 1.16(3H, d, J=6 Hz, H-6'), 1.67-1.99(2H, m, H-2'), 1.99-2.21(2H, m, H-8), 2.80-3.00(2H, m, H-10), 3.55-3.70(1H, m, H-4'), 3.99(3H, s, —OCH₃), 4.08-4.17(1H, m, H-5'), 4.60(2H, s, H-14), 4.89(1H, m, H-7), 5.28(1H, m, H-1'), 5.50(1H, s, 9-OH), 7.52-7.70(2H, m, H-2, H-3), 7.80(1H, d, J=3 Hz, H-1), 7.92-8.12(2H, m, NH₂), 13.25(1H, broad s, Ar-OH), 14.08(1H, s, Ar-OH)

EXAMPLE 2

Production of adriamycin hydrochloride without isolating 14-trifluoromethanesulfonyloxydaunomycin In a nitrogen atmosphere, 0.751 g (2.923 mmoles) of silver trifluoromethanesulfonate was added to a solution in 5 ml of DMF of 1.00 g (1.555 mmoles) of 14-bromodaunomycin hydrochloride prepared by the method described in Example 2 of U.S. Pat. No. 4,360,664 in a brown vessel, and the mixture was stirred overnight at room temperature. A solid (AgBr) which precipitated in the reaction mixture was separated by filtration and washed with DMF. The filtrate and the washing were combined.

Wafer (40 ml) was added to the mixture, and while the pH of the mixture was adjusted to 6.0 to 6.5 with 1N-NaOH, hydrolysis was carried out for 0.5 hour. The reaction mixture was diluted with water. The pH of the diluted mixture was adjusted to 3.5 with 1N-HCl, and it was washed with chloroform twice. Methanol was added to the aqueous layer, and a saturated aqueous solution of sodium hydrogen carbonate was added until the pH of the aqueous layer reached 8-9. The solution was then extracted with chloroform. The organic layer was washed with a saturated aqueous solution of sodium chloride, and dried over anhydrous sodium sulfate. The solvent was removed by concentration, and 1.05 ml of 1N-HCl (in CH₃OH, f=1.013) was added. Furthermore, chloroform was added to precipitate adriamycin hydrochloride. The precipitate was filtered, and the filtrate was washed with chloroform:methanol (10:1) and dried to give 0.632 g of adriamycin hydrochloride (94.7%, yield from 14-bromodaunomycin hydrochloride 70.1%). This product agreed in physicochemical properties with the product obtained in Example 1.

EXAMPLE 3

Differences of the alkaline hydrolysis of 14-bromodaunomycin and the alkaline hydrolysis of 14-acetoxydaunomycin from the acid hydrolysis of 14-trifluoromethanesulfonyloxydaunomycin Method It was reported that adriamycin is weak to alkalies [F. Arcamone, Topics in Antibiotic Chemistry, vol. 2, edited by P. G. Sammes, Ellis Horwood Limited (1978), p. 172].

14-Bromodaunomycin was hydrolyzed with sodium phosphate, and 14-acetoxydaunomycin, with an aqueous solution of sodium hydrogen carbonate as the alkaline hydrolysis method described in U.S. Pat. No. 3,803,124.

Separately, the acid hydrolysis of 14-trifluoromethanesulfonyloxydaunomycin was carried out using water and a 0.05M phosphate buffer (pH 6.0).

The formation of the hydrolyzates by these methods was detected by a TLC scanner, and the hydrolyzates were evaluated.

Reaction conditions

| (1) Alkaline hydrolysis methods<br>I-a: Hydrolysis of 14-bromodaunomycin<br>with sodium phosphate | |
|---|---|
| 14-Bromodaunomycin hydrochloride | 0.1 g |
| 0.5 M Na₃PO₄ | |
| Water | 10 ml |
| Acetone | 10 ml |
| Adjusted to pH 11 | |
| I-b: Hydrolysis of 14-acetoxydaunomycin<br>in an aqueous soution of sodium<br>hydrogen carbonate | |
| 14-Acetoxydaunomycin | 0.01 g |
| Acetone/CH₃OH (2:1) | 5 ml |
| 5 % Aqueous solution of NaHCO₃ | 1 ml |
| Water | 3 ml |
| (2) Acid hydrolysis of 14-trifluoromethane<br>sulfonyloxydaunomycin<br>2-1: Hydrolysis in H₂O | |
| 14-Trifluoromethanesulfonyloxydaunomycin<br>hydrochloride | 0.2 g |
| H₂O | 20 ml |
| pH 2.4 | |
| 2-2: Hydrolysis with 0.05 M phosphate<br>buffer (pH 6.0) | |
| 14-Trifluoromethanesulfonyloxydaunomycin<br>hydrochloride | 0.2 g |
| 0.05 M PBS (pH 6.0) | 20 ml |
| pH 4.2 | |

TLC conditions

TLC plate: Merck Art 5715
Developing system: CHCl₃:CH₃OH:CH₃COOH=20:4:1
TLC scanner: Shimazu TLC scanner CS-930
Wavelength: 495 nm Results The results are given in the following Table.

| Method of hydrolysis | pH | TLC scanner analysis values | | Starting material | Reaction time |
|---|---|---|---|---|---|
| | | Hydrolyzate | ADM | | |
| Alkaline hydrolysis | | | | | |
| (1-a) sodium phosphate | 11 | 30.4 | 62.0 | 7.5 | 50 minutes |

-continued

| Method of hydrolysis | pH | TLC scanner analysis values | | | Reaction time |
|---|---|---|---|---|---|
| | | Hydro-lyzate | ADM | Starting material | |
| (1-b) 5 % NaHCO$_3$ aq. | | 36.0 | 46.0 | 9.6 | 18 hours |
| Acid hydrolysis | | | | | |
| (1-a) H$_2$O | 2.4 | 4.5 | 81.7 | 13.7 | 25 hours |
| (1-b) 0.05 M.PBC (pH 6.0) | 4.2 | 6.1 | 83.9 | 9.9 | 70 minutes |

COMPARATIVE EXAMPLE 1

An attempt was made to produce adriamycin hydrochloride in accordance with Example 1 of U.S. Pat. No. 3,803,124.

When 14-bromodaunomycin was prepared in accordance with Example 1 of U.S. Pat. No. 3,803,124, its yield was 18.3%. Accordingly, the conditions were modified as follows:

Distilled water (70 ml) was added to a solution in 150 ml of methanol of 14-bromodaunomycin hydrochloride (1.0 g, 1.555 mmoles) prepared by the method described in U.S. Pat. No. 4,360,664, and under a nitrogen atmosphere, 0.1N NaOH was added at 20° C. until the pH of the solution reached 10.3. At this pH, 14-bromodaunomycin hydrochloride was hydrolyzed for 20 minutes. Distilled water (130 ml) was added to the reaction solution, and the mixture was extracted with chloroform five times. The organic layers were combined and washed with a saturated aqueous solution of sodium chloride, and dried over anhydrous sodium sulfate. The solvent was removed by concentration, and 1.86 ml of 0.6N HCl (in CH$_3$OH, f=0.967) was added to the residue. Ether (70 ml) was further added to precipitate adriamycin hydrochloride. The precipitate was filtered and the filtrate was washed with 60 ml of ether and dried to give 0.6766 g (HPLC relative purity: 58%) of adriamycin hydrochloride. Attempts were made to crystallize the resulting adriamycin hydrochloride from a propanol/methanol solvent, a chloroform/methanol solvent or a methylene chloride/methanol solvent in accordance with the description of Example 1 of the above U.S. Patent. But because of its low purity, it could not be crystallized. The purity of the resulting adriamycin hydrochloride could not be increased.

COMPARATIVE EXAMPLE 2

As in Comparative Example 1, when Example 1 of U.S. Pat. No. 3,803,124 was repeated, adriamycin hydrochloride of high purity could not be obtained (the yield was only 18.3%). Hence, the operating conditions were changed to some extent as shown below, and an attempt was made to produce adriamycin hydrochloride.

14-Bromodaunomycin (1.0 g, 1.555 mmoles) prepared in accordance with the method of Example 2 of U.S. Pat. No. 4,360,664 was dissolved in 200 ml of distilled water. In a nitrogen atmosphere, 0.1N NaOH was added to the solution at 20° C. until the pH of the solution reached 10.3, and hydrolysis was carried out at this pH for 20 minutes. Methanol (150 ml) was added to the reaction solution, and the mixture was extracted with chloroform five times. The organic layers were combined, washed with a saturated aqueous solution of sodium chloride, and dried over anhydrous sodium sulfate. The solvent was removed. The residue was dissolved in chloroform/methanol (10:1), and 3.01 ml of 0.6N HCl (in CH$_3$OH, f=0.967) was added. The mixture was concentrated and allowed to stand at a low temperature. The resulting precipitate was separated by filtration, washed with chloroform and dried to give 0.2152 g of adriamycin hydrochloride (HPLC relative purity: 94.1%; yield: 23.9%).

COMPARATIVE EXAMPLE 3

An attempt was made to produce adriamycin hydrochloride via 14-acetoxydaunomycin in accordance with the method described in Example 2 of U.S. Pat. No. 3,803,124.

When Example 1 of U.S. Pat. No. 3,803,124 was repeated 14-bromodaunomycin was obtained in a yield of 18.3%.

0.6 g (0.944 mmole) of 14-bromodaunomycin hydrochloride prepared in accordance with the method of Example 2 of U.S. Pat. No. 4,360,664 was suspended in 200 mmoles of anhydrous acetone, and 1.8 g of molten potassium acetate was added. The mixture was heated under reflux for 45 minutes. The insoluble matter was removed by filtration, and the filtrate was concentrated to dryness under reduced pressure. The residue was dissolved in chloroform, and ether was added. The resulting precipitate was filtered to give 0.429 g of a solid. The solid was purified on a silica gel column (Merck Art 7734; methylene chloride/methanol/water=100/20/2) to give 0.247 g of 14-acetoxydaunomycin. The resulting 14-acetoxydaunomycin (0.1 g) was dissolved in 30 ml of acetone/methanol (2/1) and 10 ml of a 5% aqueous solution of sodium hydrogen carbonate was added. The mixture was stirred for 3 hours. The reaction mixture was diluted with water, and extracted with chloroform. The extract was washed with a saturated aqueous solution of NaCl, then dehydrated over anhydrous sodium sulfate, and concentrated under reduced pressure 0.6N HCl/methanol were added, and ether was further added in a threefold amount. The resulting precipitate was filtered to give 57.4 mg of adriamycin hydrochloride (HPLC relatively purity 72.4%; total yield from 14-Br-DM 18.9%).

We claim:
1. 14-Trifluoromethanesulfonyloxydaunomycin represented by the following formula

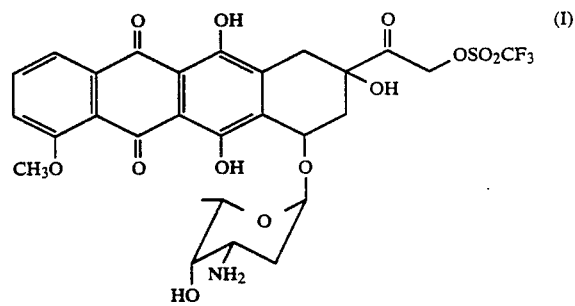

or its salt.

* * * * *

UNITED STATES PATENT AND TRADEMARK OFFICE
CERTIFICATE OF CORRECTION

PATENT NO. :    4,997,922
DATED       :    March 5, 1991
INVENTOR(S) :   Takeo YOSHIOKA et al.

It is certified that error appears in the above-identified patent and that said Letters Patent is hereby corrected as shown below:

ON TITLE PAGE:    please insert

--[30]        Foreign Application Priority Data

Sept. 6, 1988  [JP]        Japan .................... 63-221474/88
Nov. 22, 1988  [JP]        Japan .................... 63-293473/88

Signed and Sealed this

First Day of September, 1992

*Attest:*

DOUGLAS B. COMER

*Attesting Officer*    *Acting Commissioner of Patents and Trademarks*